United States Patent [19]

Kikuchi et al.

[11] 4,049,455
[45] Sept. 20, 1977

[54] LIGHT-SENSITIVE SILVER HALIDE PHOTOGRAPHIC MATERIAL

[75] Inventors: Shoji Kikuchi; Ryosuke Satoh; Takaya Endo; Katsunori Kato, all of Hino, Japan

[73] Assignee: Konishiroku Photo Industry Co., Ltd., Tokyo, Japan

[21] Appl. No.: 708,298

[22] Filed: July 26, 1976

[30] Foreign Application Priority Data

Aug. 15, 1975   Japan .................................. 50-99274

[51] Int. Cl.² .......................... G03C 1/48; G03C 1/06
[52] U.S. Cl. ......................................... 96/76 R; 96/95
[58] Field of Search .................. 96/3, 29 R, 66.3, 95, 96/76

[56] References Cited

U.S. PATENT DOCUMENTS

| | | | |
|---|---|---|---|
| 3,632,345 | 1/1972 | Marx et al. | 96/95 |
| 3,698,898 | 10/1972 | Grasshoff | 96/3 |
| 3,928,041 | 12/1975 | Fujiwhara et al. | 96/66.3 |

*Primary Examiner*—Mary F. Kelley
*Attorney, Agent, or Firm*—Flynn & Frishauf

[57] ABSTRACT

A light-sensitive silver halide photographic material containing a new development inhibitor releasing compound. The said compound has no hydrogen atom at the carbon atom which is adjacent to the carbonyl group and capable of coupling to an oxidation product of a color developing agent on the development.

6 Claims, No Drawings

LIGHT-SENSITIVE SILVER HALIDE PHOTOGRAPHIC MATERIAL

This invention relates to a light-sensitive silver halide photographic material.

It has long been known that a compound which releases development inhibitor on a development depending on the density of image (hereinafter, this compound will be referred to as a development inhibitor releasing compound) is incorporated into a light-sensitive photographic material. This compound is a type of compound which generally reacts with oxidation products of color developing agents and release development inhibitors and as representative compounds there have been known the so-called DIR couplers which have radicals forming compounds showing development-inhibiting effect when split off from the coupling position. These compounds are disclosed, for example in BP Pat. No. 953,454 and U.S. Pat. No. 3,227,554.

When these compounds couple with oxidation products of color developing agents, the couplers themselves form dyes and release development inhibitors. On the other hand there are known compounds which release development inhibitors but form no dyes when they react with oxidation products of color developing agents such as are disclosed in U.S. Pat. No. 3,632,345, Japanese Laid Open patent publication Nos. Sho 49-84439/1976, Sho 49-77635/1974, Sho 49-104630/1974, Sho 50-20725/1975 and Sho 51-6724 (1976). Further there are known so-called DIR hydroquinones in which hydroquinone and development inhibitors are combined.

These development inhibitor releasing compounds are used generally for the following objects: that is, they are characterized in that they release development inhibitors on development depending on the image density. The released inhibitors, in an emulsion layer, have a so-called intra-image effect such as control of tone, fine grainess of image, and improvement in sharpness of image because they inhibit development depending on the density of image. They, when diffused into other layers, have the so-called masking action of inhibiting the development of said other layers in correspondence to the image density of the original layer and, on monochromatic exposure, have the so-called inter-image effect of improvement of color caused by inhibiting development in other layers. They are expected to have both intra- and inter-image effects. Known development inhibitor releasing compounds, when applied to light-sensitive color photographic materials, have sufficiently effective inter- and intra-image effects, but some problems in their storage stability. That is, light-sensitive color photographic materials containing known development inhibitor releasing type compounds described above have defects in that, when stored in a state of high temperature or high temperature and high humidity, they cause a decrease in sensitivity.

An object of this invention is to provide development inhibitor releasing compounds characterized in that they have sufficient development inhibiting effects and do not cause a decrease in sensitivity during storage of light-sensitive silver halide photographic materials containing them.

Another object is to provide novel development inhibitor releasing compounds having high inter- and intra-image effects.

A further object is to provide light-sensitive silver halide photographic materials containing novel development inhibitor releasing compounds improved in storage stability in the state of high temperature, or high temperature and high humidity. Other objects will be clear from the description mentioned hereinafter.

The development inhibitor releasing compounds according to this invention are those which, on reaction with oxidation products of color developing agents, form substantially colorless compounds and simultaneously release development inhibitors and have the following formula:

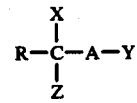

wherein A represents a sulfur or selenium atom;

X represents a 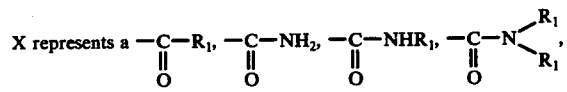

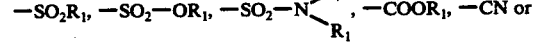

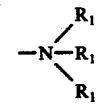

radical wherein $R_1$ represents an alkyl, aryl, or 5–6 membered hetrocyclic radical; R represents an alkyl, aryl, 5–6 membered heterocyclic radical, a -A-Y radical, a halogen atom or a -O-W radical wherein W represents an alkyl, aryl, acyl or 5–6 membered heterocyclic radical; Z represents a halogen atom; Y represents a radical forming a development inhibitor with the sulfur or selenium atom when the thioether or selenoether bond is split off.

More particularly in the formula, $R_1$ represents (1) a saturated or unsaturated aliphatic radical having up to 18 carbon atoms, preferably up to 5 carbon atoms, which can be substituted with a hydroxy, alkoxy or aryl radical; (2) an aryl radical, preferably a phenyl or naphthyl radical, which can be substituted with an alkyl radical having up to 18 carbon atoms, an alkoxy or acylamino radical, a halogen atom, a nitro or nitrile radical; (3) a 5–6 membered heterocyclic radical which contains one or more heteroatoms of a nitrogen, oxygen, sulfur or selenium atom and which can be condensed with a benzene or naphthalene ring; two of $R_1$, for example, in the grouping

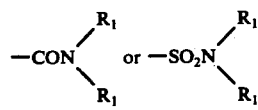

can form together a 5–6 heterocyclic ring containing nitrogen, such as piperidine, pyrrolidine and morpholine; R represents (1) an alkyl radical having preferably up to 18 carbon atoms; (2) an aryl radical, preferably a phenyl or naphthyl radical, which can be substituted with an alkyl radical having up to 18 carbon atoms, an alkoxy radical, a halogen atom, a nitro or nitrile radical; (3) a 5–6 membered heterocyclic radical which contains one or more heteroatoms of a nitrogen, oxygen, sulfur or selenium atom and which can be condensed with a benzene or naphthalene ring, e.g. benzoxazole, benzthiazole, benzoselenazole, naphthoxazole, naphthothiazole or naphthoselenazole; (4) a -A-Y radical; (5) a halogen atom; or (6) a -O-W radical in which W represents an alkyl radical having preferably up to 5 carbon atoms, an aryl radical, preferably a phenyl or naphthyl radical, an acyl radical, preferably lower acyl radicals such as an acetyl and propionyl or 5–6 membered heterocyclic radical which contains one or more heteroatoms of a nitrogen, oxygen, sulfur or selenium atom and which can be condensed with a benzene or naphthalene ring; Z represents a halogen atom such as a bromine and chlorine atom; Y represents a radical forming development inhibotors together with a sulfur or selenium atom when the thioether or selenoether bond is split off and its representative are as follows: heterocyclic mercapto compounds such as mercaptotetrazole compounds, e.g., 1-phenyl-5-mercaptotetrazole, 1-nitrophenyl-5-mercaptotetrazole, and 1-naphthyl-5-mercaptotetrazole, mercaptothiazole compounds, e.g. 2-mercaptobenzothiazole and 2-mercaptonaphthothiazole, mercaptoxadiazole compounds, mercaptopiperidine compounds, mercaptothiadiazole compounds, e.g. mercaptotriazine compounds, mercaptotriazole compounds; aromatic mercapto compounds such as mercaptobenzene compounds, e.g. 1-mercapto-2-benzoic acid, 1-mercapto-2-nitrobenzene and 1-mercapto-3-heptadecanoylaminobenzene; heterocyclic seleno compounds, e.g. 1-phenyl-5-selenotetrazole, 2-selenobenzoxazole, 2-selenobenzothiazole; and aromatic seleno compounds such as selenobenzene compounds, e.g. 4-(4-hydroxyphenylsulfonyl)selenophenol.

The compounds having the above formula (hereinafter referred to as the compounds of this invention) form substantially colorless compounds on reaction with oxidation products of color developing agents such as p-phenylene diamines, so that these formed compounds do not constitute a part of final image. Therefore, they have merit in that it is not necessary to use different compounds depending on applied object, for example, the kind of the applied layer and a single compound can be used in any layer or any photographic material.

The compounds of this invention are structurally similar with those disclosed in U.S. Pat. No. 3,632,345. They have a difference in that the compounds of this invention have no hydrogen atom at the carbon atom at which the radical forming a development inhibitor is attached. This difference has an important meaning. Because of the absence of a hydrogen atom at the coupling position in the art of known couplers, the reaction with the oxidation product of a color developing agent is not expected to occur.

Therefore, the compounds of this invention are similar in structure with those of known development inhibitor releasing compounds but have an essential difference and this difference plays an excellent effect in unexpected reactivity and improved storage stability.

The compounds of this invention will be illustrated by the following Exemplified compounds:

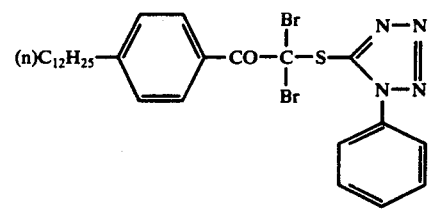

(1)

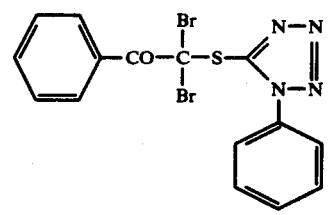

(2)

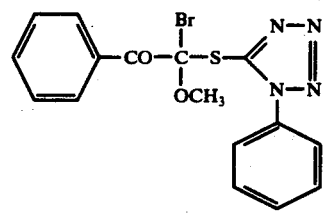

(3)

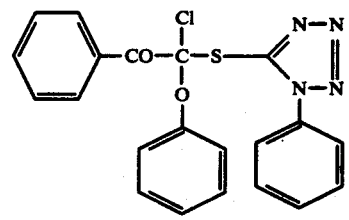

(4)

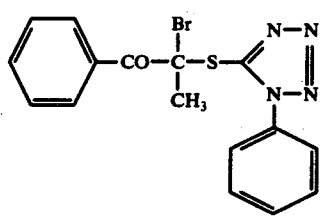

(5)

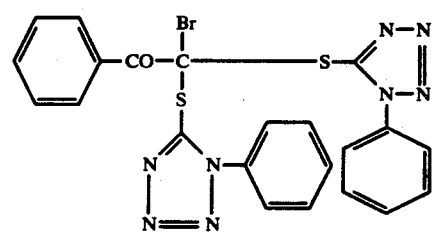

(6)

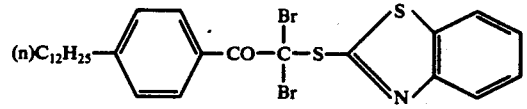

(7)

(8)

-continued

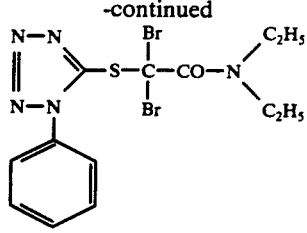
(9)

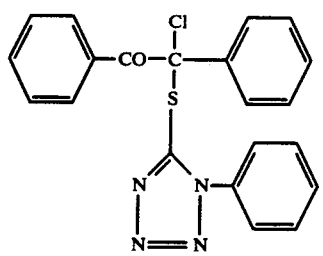
(10)

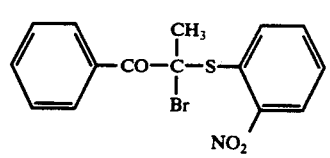
(11)

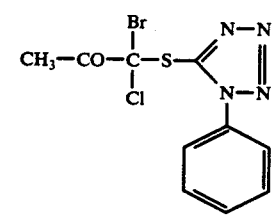
(12)

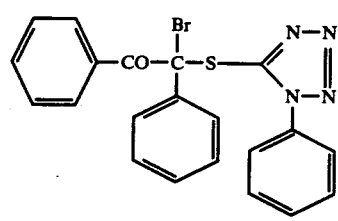
(13)

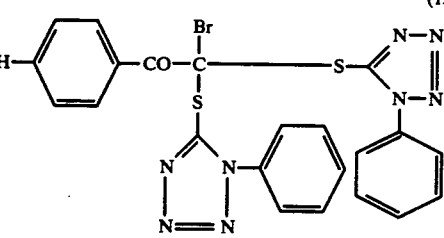
(14)

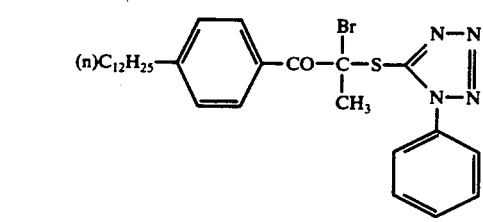
(15)

-continued

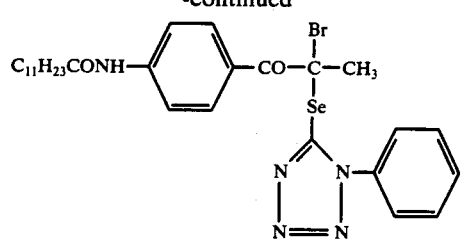
(16)

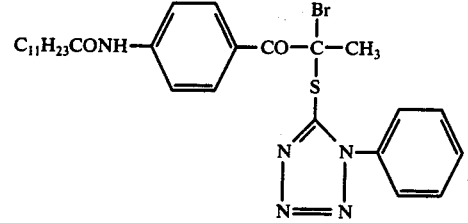

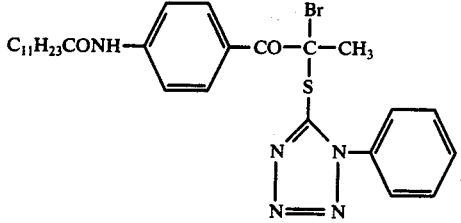
(17)

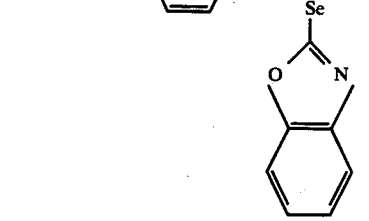

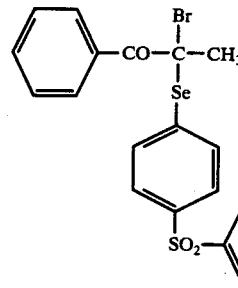
(18)

Next, representative synthesizing method of these compounds will be described, and other compounds can be easily prepared according to these synthesis.

Synthesis Example 1 Synthesis of Exemplified Compound (2)

To 1 l. of acetic acid was dissolved 37.5 g of ω-bromo-ω-(1-phenyl-tetrazolythio)-acetophenone and 24 g of bromine in acetic acid was dropwise added to the solution with reflux and stirring over one hour and the stirring was continued for further two hours. The acetic acid was distilled off under reduced pressure and the residue was separated and refined by liquid column chromatography using benzen-acetone (9:1) as solvent and silicon dioxide as carrier and recrystallized from methanol to give the desired Exemplified compounds (2).

Synthesis Example 2 Synthesis of Exemplified Compound (9)

To 500 ml. of chloroform was dissolved 19 g of ω-phenyl-ω-(1-phenyl-5-tetrazolylthio)-acetophenone and 10 g of sulfuryl chloride in 500 ml. of chloroform was added dropwise with stirring and refluxing over one hour and the mixture was stirred for further one hour. The chloroform was distilled off under reduced pressure and hexane was added to the residue and the solidified residue was recrystallized from methanol to give desired Exemplified compound (9).

Synthesis Example 3 Synthesis of Exemplified Compound (6)

To 1 l. of chloroform was dissolved 46 g of ω-bis(1-phenyl-5-tetrazolylthio)-acetophenone and 24 g of bromine in 200 ml. of chloroform was added dropwise to the solution with refluxing and stirring over 1 hour and after completion of the dropping the solution was stirred for two hours. The chloroform was distilled off under reduced pressure. The residue was treated with liquid column chromatography and recrystallized from alcohol to give desired Exemplified compound (6).

Synthesis Example 4 Synthesis of Exemplified Compound (15)

α-(1-phenyl-5-tetrazolylseleno)-4-laurylaminopropiophenone which was obtained by condensing the potassium salt of α-bromo-4-laurylaminopropiophenone with 1-phenyl-5-selenotetrazole in acetonitrile was brominated is chloroform as in Synthesis Example 3 to give the desired compound.

To confirm these compounds thus synthesized, elementary analyses of these compounds on sulfur or selenium were carried out and were tabulated as follows:

| Exemplified | Elementary analysis (S or Se) % | |
|---|---|---|
| Compound | Calculated | Found |
| (1) | 5.15 | 5.02 |
| (2) | 7.06 | 7.05 |
| (3) | 7.91 | 8.12 |
| (4) | 7.58 | 7.52 |
| (5) | 8.24 | 8.09 |
| (6) | 11.89 | 12.21 |
| (7) | 10.49 | 10.45 |
| (8) | 6.95 | 6.64 |
| (9) | 8.20 | 8.32 |
| (10) | 8.76 | 8.52 |
| (11) | 9.22 | 8.98 |
| (12) | 7.10 | 7.11 |
| (13) | 8.75 | 8.95 |
| (14) | 5.75 | 5.96 |
| (15) | 12.46 | 12.25 |
| (16) | 5.47 | 5.32 |
| (17) | 13.02 | 13.11 |
| (18) | 6.16 | 6.34 |

The compounds of this invention, which are synthesized in the above manner, can be used in various kinds of light-sensitive silver halide photographic materials such as black-white, color and pseudo-color photographic materials, and also applied to light-sensitive silver halide photographic materials of various uses, such as ordinary black-white, printing black-white, X-ray, electron-ray, high resolution black-white, ordinary color, color X-ray and diffusion transfer color photographic materials. The silver halides used in this case are silver chloride, silver bromide, silver iodide, and mixed silver halides such as silver chloro-bromide, silver iodo-bromide, and silver chloro-iodo-bromide. These can be prepared according to any processes adopted for preparation of the so-called conversion emulsions or Lippman's emulsions, depending upon kinds of the photographic materials used. The kind, grain size, content and mixing ratio of the silver halides vary depending on the nature of the photographic materials. In the case of relatively low speed and fine grain photographic materials, the silver halides are compound mainly of silver chloride, while in the case of relatively high speed photographic materials, the content of silver chloride is low. For use in direct positive photographic materials, the silver halides are fogged either optically or chemically. Further, these silver halides may be chemically sensitized with one or more sensitizers such as active gelatin, sulfur sensitizers, e.g. allylthiocarbamide, thiourea and cystine, selenium sensitizers, noble metal sensitizers, e.g. potassium chloroaurite, potassium aurithiocyanate, potassium chloroaurate or 2-aurosulfobenzothiazole, and ruthenium, rhodium, palladium and iridium sensitizers, e.g. ammonium chloropalladate, potassium chloroplatinate and sodium chloropalladate, which have been known to act as sensitizers or antifogants depending on the amounts thereof. The silver halides may be chemically sensitized with the use of a single or combination of these sensitizers.

The silver halides may be applied on a support in the form of the so-called silver halide emulsions dispersed in a binder comprising one or more of gelatin, other colloidal substances such as colloidal albumin, cellulose derivatives or synthetic resins such as polyvinyl compound, if necessary through subbing layer, inter layer, etc. The silver halide emulsions may be optically sensitized with, for example, cyanine or merocyanine dyes. In color photographic materials, there are used three kinds of silver halide emulsions having different sensitive wave-length regions. Furthermore, the silver halide emulsions may be stabilized with triazoles, azaindenes, quaternary benzothiazolium compounds, zinc or cadmium compounds, and may contain sensitizing compounds such as quaternary ammonium salts or polyethylene gylcols. The emulsions may further contain suitable gelatin plasticizers such as dihydroxy alkanes, e.g. glycerin and 1,5-pentanediol, esters of ethylenebisglycolic acid, bisethoxydiethyleneglycol succinate, acid amides of acrylic acid and latexes; gelatin hardeners such as formaldehyde, halogen-substituted fatty acids, e.g. mucobromic acid and mucochloric acid, compounds having acid anhydride groups, dicarboxylic acid chlorides, biesters of methanesulfonic acid, and sodium bisulfite derivatives of dialdehydes whose aldehyde groups are separated by 2 to 3 carbon atoms; coating aids such as saponins and sulfosuccinates; and various photographic additives. Particularly in the case of inner color photographic materials in which couplers are contained in the materials, the emulsion may contain couplers such as 5-pyrazolone type magenta couplers, naphthol or phenol type cyan couplers and yellow couplers having active methylene groups interposed between two carbonyls, which may be the so-called 2-equivalent or 4-equivalent couplers, and may also contain masking couplers which have, for example, arylazo group in the coupling position. The said masking couplers are preferably used in combination with the so-called colorless couplers, which are colorless before color development. In the case of using the so-called protect type couplers, the emulsion may contain coupler solvents as dispersing agents. In order to enhance the photographic properties, the emulsion may further contain, in combination with various couplers, the so-called competing couplers which form leuco-dyes. In the case of color photographic materials, the emulsions may contain, if necessary, ultraviolet absorbers, fluorescent brightening agents, etc.

Such silver halide emulsions are applied on a support, if necessary, through subbing layer, inter layer, etc., to prepare light-sensitive silver halide photographic materials. The supports used in this case are paper, laminated paper, glass, and cellulose acetate, cellulose nitrate, polyester, polyamide films and sheets and may be selected according to the use object of the photographic materials. Fundamentally, the photographic material is composed of a support and at least one photosensitive layer. As mentioned above, however, the photographic material may have, depending on the kind of photographic materials, a subbing layer, inter layer, filter layer, anti-curling layer, protective layer, etc. which may properly be combined with each other. Further, the photosensitive layer itself may be composed of multilayers of high sensitivity and relatively low sensitivity in the same or different wavelength region. Further, each layer may contain different additives such as are contained in aforesaid emulsions. Each layer may contain various additives depending on its intended object, for example, the filter layer may contain a filter dye, and the protective layer may contain a film property improving agent and an antistatic agent. The diffusion transfer photographic materials, for example, may have an inter layer containing a physical development nucleus as one embodiment.

The light-sensitive silver halide photographic materials thus obtained is developed in the presence of a compound of this invention to obtain such excellent properties as mentioned above and, as a preferable embodiment, the said compound is incorporated into the photographic emulsion. In this case, the compound of the diffusible type may be incorporated into one or more of an emulsion layer, inter layer, protective layer, etc., and the compound of the non-diffusible type is preferably incorporated into one or more of an emulsion layer or adjacent layer thereto.

In preparing photographic materials incorporated with the compounds of this invention, the compounds can be incorporated in any form into a coating liquid for forming a layer of the photographic material. That is, the diffusible compound may be incorporated in the form of a solution, e.g. an aqueous alkaline solution, while the non-diffusible compound may be incorporated in the form of an emulsion, e.g. an emulsion in the said coupler solvent. The coupler solvents are, in general, water-immiscible high boiling organic solvents such as di-n-butyl phthalate, benzyl phthalate, triphenyl phosphate, tri-o-cresyl phosphate, monophenyl-di-p-t-butylphenyl phosphate or mixed solvents thereof with low boiling organic solvents such as methyl isobutyl ketone, $\beta$-ethoxyethyl acetate, methoxytriglycol acetate, acetone, methyl acetone, methanol, ethanol, acetonitrile, dioxane, dimethylformamide, ethyl acetate, isopropyl acetate and chloroform. The latter low boiling solvents can be used in place of the former high boiling solvents. These organic solvents can be used either singly or in the form of a mixture of two or more of them.

The compounds of this invention can be used in various forms as above mentioned and give excellent results compared with known development inhibitor releasing compounds. The compounds can be contained in photographic treatment liquids, but the effects are particularly marked when the compounds are incorporated into photographic materials. The amount of the compounds used in this invention varies depending on the application procedure, desired object and the intended effect, but its amount incorporated in emulsions is preferably in a range of 0.1 to 10 g per kg of the emulsion. In case where they are used in the same amount as in known development inhibitor releasing type compounds, the image effect obtained is remarkably excellent compared with that obtained in said known compounds and in case where the same effect as that obtained in the said known compounds is expected, they are used in an extremely small amount.

The light-sensitive silver halide color photographic materials containing the compounds of this invention can be developed either by a color developer containing couplers or not. For example, the color developer containing couplers used is as follows:

| | |
|---|---|
| N-ethyl-N-$\beta$-methanesulfonamidoethyl-3-methyl-4-aminoaniline | 5.0 g |
| Sodium sulfite | 2.0 g |
| Benzyl alcohol | 3.5 ml |
| Sodium carbonate | 82. g |
| Potassium bromide | 1.2 g |
| Coupler | 0.005 mole |
| A compound of this invention | 2.0 g |
| Water to make | 1.0 l. | and the color developer containing no couplers used is as follows:

| | |
|---|---|
| N-ethyl-N-$\beta$-methanesulfonamidoethyl-3-methyl-4-aminoaniline sulfate | 5.0 g |
| Sodium sulfite (Anhydrous) | 2.0 g |
| Benzyl alcohol | 3.8 g |
| Sodium carbonate (1 hydrate) | 50. g |
| Potassium bromide | 1.0 g |
| Potassium hydroxide | 0.55 g |
| A compound of this invention | 2.5 g |
| Water to make | 1 l. |

The color developing agents used for color treatment in this invention are preferably aromatic primary amine compounds and particularly those of p-phenylenediamines such as N,N-diethyl-p-phenylenediamine, N-ethyl-N-$\omega$-sulfobutyl-p-phenylenediamine, 2-amino-5-diethylaminotoluene and p-amino-N-ethyl-N-$\beta$-hydroxyethylaniline. The compounds of this invention are preferred to be coexistent with one or more of the said color developing agents on developing the photographic materials. As a typical embodiment, there is a procedure of developing the compounds of this invention by incorporating the non-diffusible development inhibitor releasing compound of this invention into a specific layer of the photographic material and by making the diffusible development inhibitor releasing compounds of this invention contained in a developer.

The silver halide photographic material thus developed is then subjected to an ordinary photographic treatment comprising a suitable combination of steps selected from, for example, stopping, stop-fixing, fixing, bleaching, bleach-fixing, stabilizing, water-washing and drying steps.

This invention will be illustrated by the following examples, but they are not meant to limit the scope of this invention.

EXAMPLE 1

Samples 1, 2, 3 and 4 were prepared as follows:

Sample 1

7.2 g of Exemplified compound (1) and 15 g of magenta coupler - 1-(2,4,6-trichlorophenyl)-3-{3-[2,4-di-t-amylphenoxy) acetamido]benzamido}-5-pyrazolone were dissolved in 30 ml of ethyl acetate and 20 ml of dibutyl phthalate and this solution was mixed with 20 ml of a 10% aqueous solution of Alkanol B (prepared by E. I. du Pont) and 200 ml of a 5% aqueous gelatin solution. This mixture was emulsified and dispersed by a colloidal mill. This dispersed liquid was added to 1 kg of green sensitive silver bromo-iodide emulsion and, after dispersion, this dispersed liquid was coated on a cellulose triacetate film base and dried.

Sample 2

This sample was prepared by the same manner as in sample 1 except that 7.0 g of Exemplified compound (6) was used instead of Exemplified compound (1).

Sample 3

This sample was prepared in the same manner as in sample 1 except that 7.0 g of p-dodecyl-ω-(1-phenyl-5-tetrazolylthio)acetophenone was used instead of Exemplified compound (1).

Sample 4

This sample was prepared in the same manner as in sample 1 except that 7.0 g of α,α-bis(1-phenyl-5-tetrazolylthio)acetophenone was used instead of Exemplified compound (6) in sample 2.

These samples were treated at 50° C and at a humidity of 30% for 3 days (hereinafter, referred to as DT treatment) and at 55° C and at a humidity of 80% for 3 days (hereinafter, referred to as HT treatment), then exposed through an usual optical wedge together with the untreated samples, developed with the following developer and fixed by an usual treatment:

| | |
|---|---|
| N,N-diethyl-p-phenylenediamine hydrochloride | 2 g |
| Anhydrous sodium sulfite | 2 g |
| Sodium carbonate (1 hydrate) | 82 g |
| Potassium bromide | 2 g |
| Water to make | 1 l. |

The sensitivity and fog measured in respective samples were listed in Table 1.

Table 1

| Sample | Untreated | | DT treatment | | HT treatment | |
|---|---|---|---|---|---|---|
| | Sensitivity | Fog | Sensitivity | Fog | Sensitivity | Fog |
| 1 | 70 | 0.06 | 68 | 0.05 | 70 | 0.07 |
| 2 | 65 | 0.05 | 61 | 0.05 | 64 | 0.06 |
| 3 | 100 | 0.09 | 83 | 0.08 | 87 | 0.12 |
| 4 | 98 | 0.08 | 78 | 0.07 | 81 | 0.11 |

The sensitivity in Table 1 was expressed in a relative sensitivity in which the sensitivity of the untreated sample 3 was defined as 100. Table 1 shows that samples 1 and 2 had little desensitivity (a very little decrease ratio of the sensitivity to that of the untreated sample) and excellent storage stability either in DT treatment or in HT treatment compared with samples 3 and 4.

EXAMPLE 2

Samples 5 and 6 were prepared as follows:

Sample 5

2 g of Exemplified compound (5) and 15 g of magenta coupler - 1-(2,4,6-trichlorophenyl)-3-[3-(2,4-di-t-amylphenoxyacetamido)benzamido]-5-pyrazolone were dissolved in 30 ml of ethyl acetate and 15 ml of dibutyl phthalate and this solution was mixed with 20 ml of a 10% Alkanol B (prepared by E. I. du Pont) aqueous solution and 200 ml of a 5% gelatin aqueous solution and emulsified and dispersed with a colloidal mill. This dispersed liquid was added to 1 kg of green sensitive silver iodobromide emulsion and, after dispersion, coated on a cellulose triacetate film base and dried.

Sample 6

This sample, as control sample, was prepared in the same manner as in sample 5 except that 1.6 g of α-(1-phenyl-5-tetrazolylthio)propiophenone was used instead of Exemplified compound (5).

These samples 5 and 6 were treated in the same manner as in Example 1 after light wedge-exposure. In both cases, the images composing of magenta dyes were formed. The sensitivity was the same in both cases but γ value in sample 6 was 0.9 while that in sample 5 was 0.5.

The image of sample 6 was composed of more finer grains than those in sample 5.

After DT treatment or HT treatment according to the conditions in Example 1, the sensitivity in both samples were measured. The results were listed in Table 2.

Table 2

| Sample | Untreated | DT treatment | HT treatment |
|---|---|---|---|
| 5 | 85 | 81 | 84 |
| 6 | 100 | 85 | 83 |

In Table, the sensitivity was expressed in a relative sensitivity in which the sensitivity of sample 6 was defined as 100. Table 2 shows that sample 5 had substantially no desensitivity and had excellent storage stability.

EXAMPLE 3

Samples 7 and 8 were prepared as follows.

Sample 7

17 g of 2-[α-(2,4-di-t-amylphenoxy)-butylamido]-4,6-dichloro-5-methylphenol was added to 1 kg of silver iodobromide emulsion which was sensitized in red region and this mixture was coated on a triacetate base. On this red sensitive emulsion layer, a green sensitive silver halide emulsion containing 7 g of Exemplified compound (15) and 20 g of 1-(2,4,6-trichlorophenyl)-3-{3-[α-(2,4-di-t-amylphenoxy) acetamido]benzamido}-5-pyrazolone was coated and dried.

Sample 8

This sample, as control sample, was prepared in the same manner as in sample 7 except that the green sensitive layer contained only the magenta coupler and Exemplified compound (15) was not contained.

These samples 7 and 8 were wedge-exposed either with red light or with white light. Then, the samples were developed with the developer used in Example 1 in the same manner as in Example 1 and bleach-fixed by an usual method.

The results obtained showed that the γ values of cyan image obtained by red and white exposure in sample 8 were the substantially the same but the γ value of cyan image obtained by white exposure in sample 7 was clearly smaller than that obtained by red exposure. This evidences that the development inhibitor released from Exemplified compound (15) diffused into the under red sensitive layer, thus resulting in inhibiting the development of the red sensitive layer and a decrease in γ value.

These samples were also subjected to DT and HT treatment in the same manner as in Example 1 and had almost no difference. This fact confirmed that Exemplified compound (15) showed almost no desensitivity.

EXAMPLE 4

The following layers were successively coated on a cellulose triacetate film base to prepare sample 9.

The weight in the following means weight per 900 cm². Layer (1)

A red sensitive silver bromoiodide emulsion containing 440 mg of gelatine and 174 mg of the said silver halide. This emulsion contained couplers — 26.3 g of 1-hydroxy-4'-(4-t-butylphenoxy)-4-phenylazo-2-naphthoanilide and 3.27 mg of 1-hydroxy-N-α-(2,4-di-t-amylphenoxy)butyl-2-naphthoamide, and 7 mg of Exemplified compound (13).

Layer (2)

A gelatin inter layer containing 83 mg of gelatin and 5 mg of dioctylhydroquinone.

Layer (3)

A green sensitive silver bromoiodide emulsion containing 400 mg of gelatin and 243 mg of the said silver halide. This emulsion contained couplers — 24.5 mg of 1-(2,4,6-trichlorophenyl)-3-{3-[α-(2,4-di-t-amylphenoxy)acetamido]benzamido}-4-(4'-methoxyphenylazo)-5-pyrazolone and 24.3 mg of 1-(2,4,6-trichlorophenyl)-3-{3-[α-(2,4-di-t-amylphenoxy)acetamido]benzamido}-5-pyrazolone, 7 mg of Exemplified compound (13) and further 8.7 mg of dioctylhydroquinone as an antistain agent.

Layer (4)

A gelatin inter layer containing 83 mg of gelatin and 5 mg of dioctylhydroquinone.

Layer (5)

A blue sensitive silver iodobromide emulsion containing 200 mg of gelatin and 62 mg of the said silver halide. This emulsion contained a coupler — 102.5 mg of N-(p-benzoylacetamidobenzenesulfonyl)-N-(α-phenylpropionyl)-p-toluidine and further 23 mg of dioctylhydroquinone as an antistain agent.

On the other hand, control sample 10 was prepared in the same manner as in Example 4 except that Exemplified compound (13) was not contained in the above red and blue sensitive layers.

These samples 9 and 10 were wedge-exposed and developed at 24° C for 10 minutes with the following developer.

| | |
|---|---|
| Anhydrous sodium sulfate | 2.0 g |
| N-ethyl-N-β-methanesulfonamidoethyl-3-methyl-4-aminoaniline sulfate | 5.0 g |
| Sodium carbonate | 50.0 g |
| Sodium bromide | 0.9 g |
| Sodium hydroxide | 4.0 g |
| Sodium hexametaphosphate | 0.5 g |
| Benzyl alcohol | 4.0 ml |
| Water to make | 1 l. |

Bleaching and fixing treatments after development were carried out by an usual method.

The results obtained showed that sample 9 containing Exemplified compound (13) according to this invention was excellent in sharpness and granularity and further small in fog compared with the control sample 10. Further this sample 9 showed no desensitivity when treated with DT and HT treatments in the same manner as in example 1.

What is claimed is:

1. A light-sensitive silver halide photographic material having a support and at least a silver halide emulsion layer coated thereon, said material containing a development inhibitor releasing compound which forms substantially a colorless compound and simultaneously releases a development inhibitor on reaction with an oxidation product of a color developing agent and has the following formula:

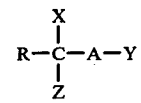

wherein A represents a sulfur or selenium atom;

X represents a 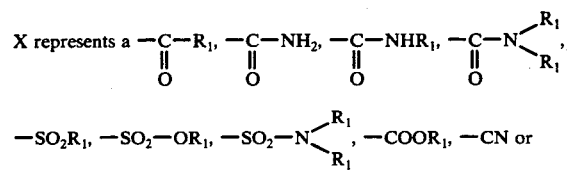

radical, wherein $R_1$ represents (1) a saturated or unsaturated aliphatic radical having up to 18 carbon atoms, (2) an aryl radical selected from the group consisting of phenyl and naphthyl, or (3) a 5–6 membered heterocyclic radical, and (4) two of $R_1$ can form together a 5–6 membered heterocyclic ring;

R represents (1) an alkyl radical having up to 18 carbon atoms, (2) an aryl radical selected from the group consisting of phenyl and naphthyl, (3) a 5–6 membered heterocyclic radical, (4) a -A-Y radical, (5) a halogen atom, or (6) a -O-W radical, wherein W represents an alkyl radical having up to 5 carbon atoms, an aryl radical selected from the group of a phenyl and naphthyl, a lower acyl radical having up to 5 carbon atoms or a 5–6 membered heterocyclic radical;

Z represents a halogen atom;

Y represents a radical forming a development inhibitor with the sulfur or selenium atom and is selected from the group consisting of a heterocyclic mercapto compound, an aromatic mercapto compound, a heterocyclic seleno compound and an aromatic seleno compound when the thioether or selenoether bond is split off.

2. A light-sensitive silver halide photographic material according to claim 1, wherein $R_1$ represents (1) an alkyl radical having up to 18 carbon atoms, (2) an aryl radical which can be substituted with an alkyl having up to 18 carbon atoms, alkoxy or acylamino radical, a halogen atom, a nitro or nitrile radical, (3) a 5–6 membered heterocyclic radical which has one or more heteroatoms selected from the group consisting of N, O, S and Se, and which can be condensed with a benzene or naphthalene ring, and (4) when $R_1$ is two or more, both of $R_1$ can form together a 5–6 membered heterocyclic ring selected from the group of piperidine, pyrrolidine and morpholine; R represents (1) an alkyl radical having up to 18 carbon atoms, (2) an aryl radical which can be substituted with an alkyl having up to 18 carbon atoms or alkoxy radical, a halogen atom, a nitro or nitrile radical (3) a 5–6 membered heterocyclic radical containing one or more heteroatoms selected from the group consisting of N, O, S and Se, and which can be condensed with a benzene or naphthalene ring, (4) a -A-Y radical, (5) a halogen atom or (6) a -O-W radical, wherein W represents an alkyl radical having up to 5 carbon atoms, an aryl radical selected from the group of a phenyl and naphthyl radical, a lower acyl radical having up to 5 carbon atoms, or a 5–6 membered heterocyclic radical which contains one or more heteroatoms selected from the group consisting of N, O, S, and Se, and which can be condensed with a benzene or naphthalene ring; Y represents a radical forming a development inhibitor selected from the group consisting of a mercaptotetrazole, mercaptothiazole, mercaptoxadiazole, mercaptopiperidine, mercaptothiadiazole, mercaptotriazine, mercaptotriazole, mercaptobenzene, selenotetrazole, selenobenzoxazole, selenobenzothiazole and selenophenol compound.

3. A light-sensitive silver halide photographic material according to claim 2, wherein $R_1$ represents a phenyl or naphthyl radical both of which can be substituted with an alkyl having up to 18 carbon atoms, alkoxy or acylamino radical, a halogen atom, a nitro or nitrile radical; R represents a phenyl or naphthyl radical both of which can be substituted with an alkyl having up to 18 carbon atoms or alkoxy radical, a halogen atom, a nitro or nitrile radical.

4. A light-sensitive silver halide photographic material according to claim 2 wherein Y represents a radical forming a development inhibitor selected from the group consisting of 1-phenyl-5-mercaptotetrazole, 1-nitrophenyl-5-mercaptotetrazole, 1-naphthyl-5-mercaptotetrazole, 2-mercaptobenzthiazole, 2-mercaptonaphthothiazole, 2-mercaptoxadiazole, 1-mercapto-2-benzoic acid, 1-mercapto-3-heptadecanoylaminobenzene, 1-phenyl-5-selenotetrazole, 2-selenobenzothiazole and 4-(4-hydroxyphenylsulfonyl)selenophenol.

5. A light-sensitive silver halide photographic material according to claim 1, wherein the development inhibitor releasing compound is selected from the group consisting

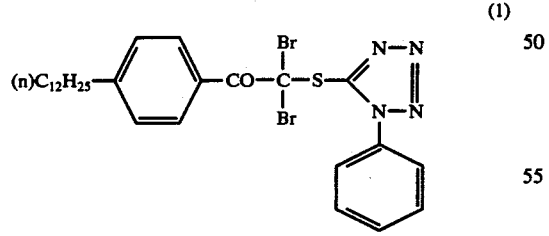

(1)

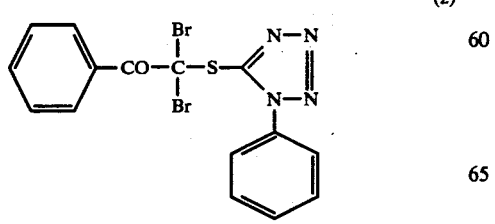

(2)

(3)

-continued

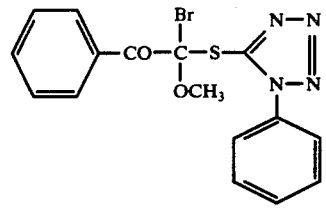

(4)

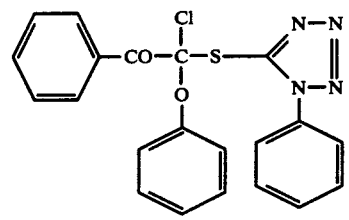

(5)

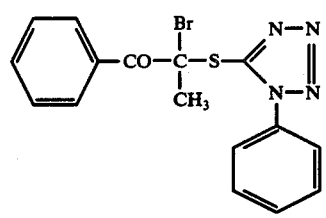

(6)

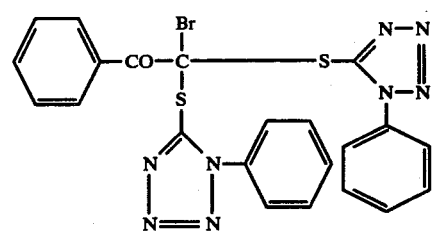

(7)

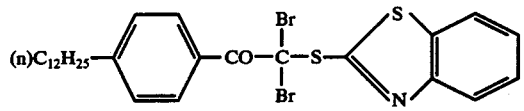

(8)

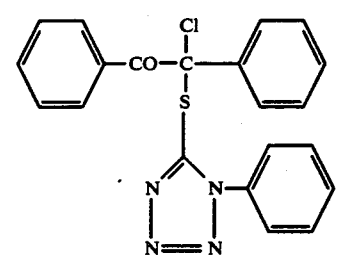

(9)

(10)

-continued
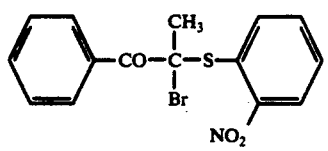
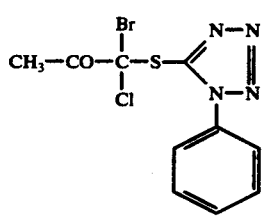 (11)
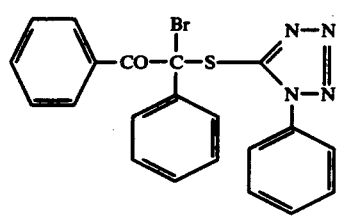 (12)
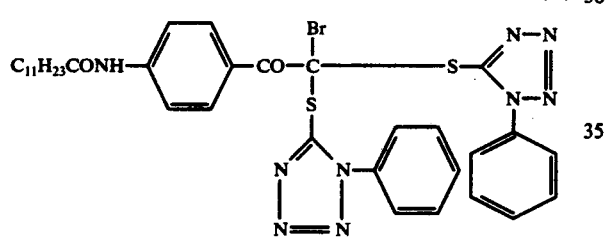 (13)
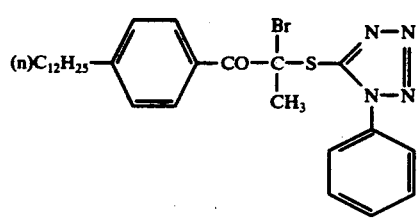 (14)
(15)
-continued
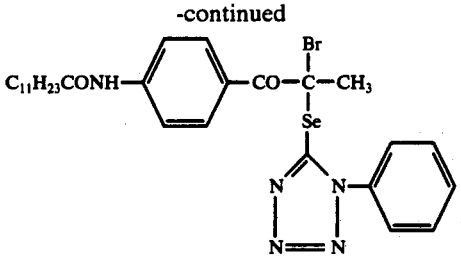
(16)
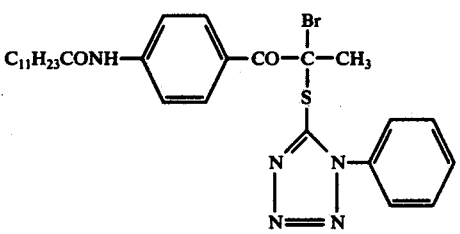
(17)
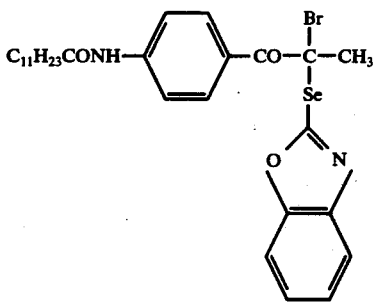
(18)
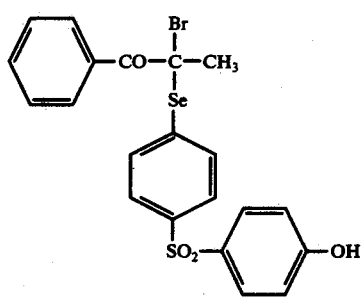
6. A light-sensitive silver halide photographic material according to claim 1, wherein the development inhibitor releasing compound is incorporated into the silver halide emulsion.
* * * * *